(12) United States Patent
Nakayama et al.

(10) Patent No.: US 8,882,788 B2
(45) Date of Patent: Nov. 11, 2014

(54) DEVICE FOR SHEET INSERTION

(71) Applicant: Fuji Systems Corporation, Tokyo (JP)

(72) Inventors: Takeshi Nakayama, Shizuoka (JP);
Akihiro Asai, Kanagawa (JP)

(73) Assignee: Fuji Systems Corporation, Tokyo (JP)

(*) Notice: Subject to any disclaimer, the term of this patent is extended or adjusted under 35 U.S.C. 154(b) by 223 days.

(21) Appl. No.: 13/661,353

(22) Filed: Oct. 26, 2012

(65) Prior Publication Data

US 2013/0110156 A1 May 2, 2013

(30) Foreign Application Priority Data

Oct. 28, 2011 (JP) ................................. 2011-236854

(51) Int. Cl.
| | | |
|---|---|---|
| *A61B 17/08* | (2006.01) | |
| *A61B 17/29* | (2006.01) | |
| *A61F 2/00* | (2006.01) | |
| *A61B 19/00* | (2006.01) | |

(52) U.S. Cl.
CPC .............. *A61B 17/29* (2013.01); *A61F 2/0063* (2013.01); *A61B 2019/4884* (2013.01); *A61F 2002/0072* (2013.01)
USPC ....................................................... 606/151

(58) Field of Classification Search
USPC ................. 128/838, 840, 850, 851, 856, 898; 606/1, 151, 213; 623/1.11, 1.12, 1.23, 623/23.72, 23.75
See application file for complete search history.

(56) References Cited

U.S. PATENT DOCUMENTS

| | | | | |
|---|---|---|---|---|
| 5,263,969 A | * | 11/1993 | Phillips | 606/213 |
| 5,304,187 A | | 4/1994 | Green et al. | |
| 5,350,387 A | * | 9/1994 | Semm | 606/151 |
| 5,464,403 A | * | 11/1995 | Kieturakis et al. | 606/1 |
| 5,503,623 A | * | 4/1996 | Tilton, Jr. | 604/13 |
| 5,919,184 A | * | 7/1999 | Tilton, Jr. | 606/1 |
| 5,957,939 A | * | 9/1999 | Heaven et al. | 606/151 |
| 6,193,731 B1 | * | 2/2001 | Oppelt et al. | 606/151 |
| 6,258,113 B1 | * | 7/2001 | Adams et al. | 606/192 |
| 6,478,803 B1 | | 11/2002 | Kapec et al. | |
| 6,695,856 B2 | * | 2/2004 | Kieturakis et al. | 606/151 |
| 7,867,222 B1 | * | 1/2011 | Tilton et al. | 606/1 |
| 8,317,808 B2 | * | 11/2012 | Levin et al. | 606/151 |
| 8,734,473 B2 | * | 5/2014 | Levin et al. | 606/151 |
| 2007/0112361 A1 | * | 5/2007 | Schonholz et al. | 606/151 |

FOREIGN PATENT DOCUMENTS

JP 2010-207417 A 9/2010

OTHER PUBLICATIONS

English translation of abstract of JP 2010-207417 A.

* cited by examiner

*Primary Examiner* — Jonathan W Miles
(74) *Attorney, Agent, or Firm* — McClure, Qualey & Rodack, LLP

(57) ABSTRACT

Disclosed is a device for sheet insertion includes: a cylindrical mantle tube of which the front and back ends are opened and the inside is formed to be a sheet receiving part and an extruding member for sheet extrusion that is inserted into the mantle tube in a state of moving in a back and forth direction that is a tube-axis direction and of rotatable, wherein the extruding member has a shaft having a longer length than that of the mantle tube and a forked sheet winding part disposed at a tip portion of the shaft, and axial slits having a size enough to insert the sheet are formed therethrough on walls facing each other at the front end of the mantle tube over approximately the same length as that of the sheet winding part.

9 Claims, 17 Drawing Sheets

DEVICE FOR SHEET INSERTION

BACKGROUND OF THE INVENTION

The present invention relates to a device for sheet insertion used for an endoscopic operation, and more particularly, to a device technology capable of simply inserting sheets such as a synthetic absorbable anti-adhesion sheet, and the like, into the body through a trocar for preventing tissues of a surgical site that is a targeted in vivo site from adhering to each other and facilitating an insertion operation. Recently, in order to stop bleeding in an excision part or to prevent an adhesion of internal organs upon a surgical operation using an endoscope, there is a case in which the synthetic absorbable anti-adhesion sheet such as a sepra film (registered trade mark), and the like, is used. Applying these sheets to the diseased sites can be simply performed in an abdominal operation having a wide surgical site, but in the endoscopic operation performed when the sheets cannot be in direct contact with the diseased sites, the operation is performed by inserting forceps or a radio knife into the body through the trocar such as a so called 'auxiliary tool for endoscope insertion', and the like, such that the sheets need to pass through the trocar so as to insert the sheets into the body.

That is, an example of inserting a sheet into the body may include, for example, a method for inserting a sheet into the body by winding the sheet around an outer circumferential surface of a forceps while holding the sheet with the forceps and then, inserting the forceps into the trocar as it is. However, the method has a problem in that the sheet cannot be skillfully applied to the diseased sites because adhesive force is activated due to the contact of various medical sheets such as the sepra film described above with moisture and the sheet has adhesive force due to an operator's hand touching to the sheet when winding the sheet around the outer circumferential surface of the forceps as described above or water or blood attached to the trocar.

As the Patent Document, a device disclosed in Japanese Patent Application Laid-Open No. 2010-207417 has been proposed. That is, the device for endoscopic operation disclosed in the Prior Patent Document includes a device body that includes a tip opening opened to the outside and receiving regions serially receiving a plurality of sheets toward the tip opening disposed therein, an extruding member that sequentially extrudes the plurality of sheets received in the receiving region within the device body outwardly from the device body through the tip opening, and a pressing part that presses the sheets to a surgical site, as described in claim 1. Further, the device having the above configuration can easily apply the sheet to the surgical site while avoiding the contact with a body fluid, facilitate the pressing of the sheet to the surgical site and continuously apply the plurality of sheets to the surgical site, in the endoscopic operation.

However, in the device disclosed in the Prior Patent Document, an end of the sheet is inserted into a vertical groove of the forceps and is gripped and then, the sheet is wound around the forceps in a cylindrical shape while the operator's hand is lightly touched to the sheet, but the sheet has adhesive force due to the operator's hand during the operation and as a result, there are problems in that the sheet is not unwound well at the time of unwinding work after the sheet is inserted into the surgical site and as indicated in Paragraph [0003], the sheet cannot be skillfully applied to the diseased sites.

SUMMARY OF THE INVENTION

Therefore, in consideration of the above problems, an object of the present invention is to provide a device for sheet insertion capable of simply inserting a sheet such as a synthetic absorbable anti-adhesion sheet, and the like, into a targeted in vivo site through a lumen of a trocar and using a trocar having a small diameter while skillfully applying the sheet, in an endoscopic operation.

In order to achieve the above object, a device for sheet insertion according to an embodiment of the present invention is a device for sheet insertion used to insert a sheet of a synthetic absorbable anti-adhesion sheet and the like into a targeted in vivo site through a lumen of a trocar in an endoscopic operation, containing: a cylindrical mantle tube of which front and back ends are opened and inside is formed to be a sheet receiving part, and an extruding member for extruding a sheet, the extruding member being inserted into the mantle tube in a state of moving in a back and forth direction that is a tube-axis direction and of rotatable, wherein the extruding member has a shaft having a longer length than the mantle tube, a forked sheet winding part disposed at a tip portion of the shaft, and a gripping part for operation disposed at a back end of the shaft, the sheet winding part is received in the mantle tube by a movement of the extruding member backward while being protruded from a front opening of the mantle tube by a movement of the extruding member forward; and the mantle tube has axial slits having a size enough to insert the sheet therethrough, which are formed on walls facing each other at the front end of the mantle tube over approximately the same length as a length of the sheet winding part.

According to the embodiment of the present invention, by the above configuration, it is possible to simply insert the sheet into the targeted site even in the endoscopic operation and to skillfully and simply perform the application or detention of the sheet after the insertion at the targeted site in the endoscopic operation, thereby shortening the operation time. Further, it can be expected that the trocar having a small diameter can also be used.

In the above description, the axial slits may be configured of any one among types in which (1) both slits facing each other are formed from the front opening of the mantle tube, (2) one slit is formed from the front opening of the mantle tube, and the other slit is formed from a position at a predetermined length from the front opening, the slits facing each other, and (3) both slits are formed from a position at a predetermined length from the front opening of the mantle tube, in particular, at least one slit of the axial slits of the pairs of the axial slits of (2) and (3) is formed from a position at a predetermined length from the tip opening of the mantle tube, that is, the walls on which the axial slits are formed connected in a circumferential direction, such that even when the mantle tube is made of, for example, synthetic resins other than metals, the mantle tube cannot be torn at by the slits as a boundary when the sheet is wound.

Further, in the above description, the device for sheet insertion includes a shaft gripping part with a sheet winding part and may have a configuration in which the gripping part includes a second shaft in which the tip extends into the mantle tube, the tip of the second shaft is pivoted with base ends of a pair of links having the same length, the tips of the links having the same length are pivoted with back ends of a pair of arms having the same length that is pivoted to the shaft having an intermediate part disposed on the extruding member, the tips of the arms are fixed with back ends of two plate parts of a sheet winding part, or when the second shaft is drawn backward, may have a configuration in which the back ends of two plate parts of the sheet winding part are pressed inwardly while the two links having the same length and the two arms having the same length are pressed inwardly, such that the tips of the two plate parts are changed from an opened state to a closed state. By the configuration, when the operator performs the endoscopic operation, it is possible to certainly insert the sheet by closing the tips of the two plate parts, thereby guiding the sheet to the targeted site without missing the sheet within a body cavity, skillfully and simply performing the application or detention of the sheet after the insertion at the targeted site, and it can be expected that the operation time can be shortened.

DETAILED DESCRIPTION OF THE INVENTION

Figure 1:
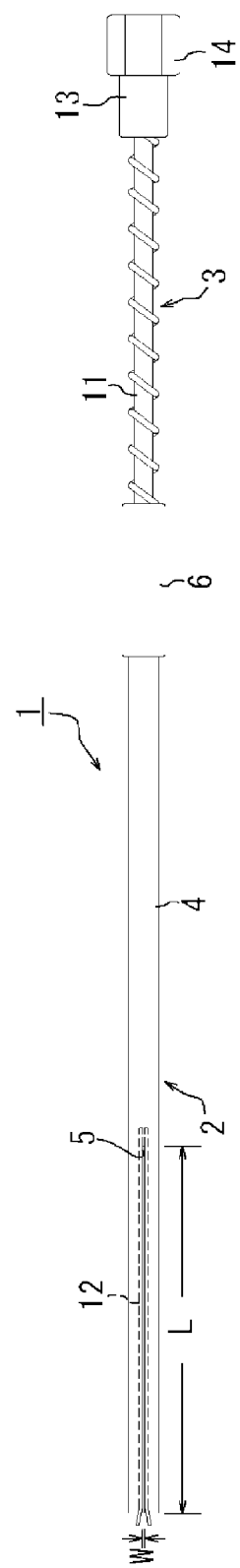
FIG. 1 is a front view illustrating a device for sheet insertion according to a first embodiment of the present invention.
Figure 2:
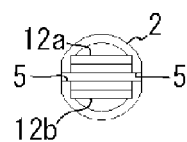
FIG. 2 is a side view seen from the left of FIG. 1.
Figure 3:
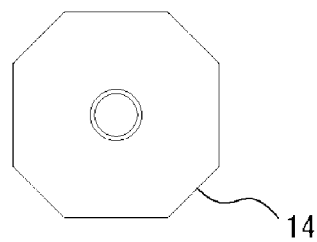
FIG. 3 is a side view seen from the right of FIG. 1.
Figure 4:
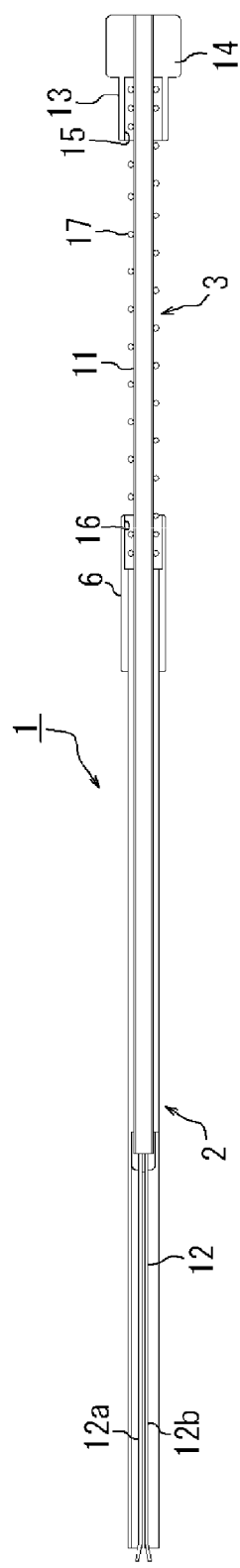
FIG. 4 is a front cross-sectional view.

A device for sheet insertion according to embodiments of the present invention will be described below with reference to the accompanying drawings.

First Embodiment

In FIGS. 1 to 4, reference numeral 1 is a device for sheet insertion, wherein the device 1 includes a mantle tube 2 as a device body (sheathe) that is made of metal, resin, and the like, and receives a film F as a synthetic absorbable anti-adhesion sheet and an extruding member 3 with a gripping part that is likewise made of metal, resin, and the like, and inserts and winds the film F into the mantle tube 2 and extrudes the wound film F out of the mantle tube 2, and has a flexible property as a whole. The film F, which is made of a resin sheet having a somewhat elastic force, prevents tissues of a surgical site that is a targeted in vivo site from adhering to each other as a main object, and has a quadrangular shape illustrated in FIGS. 7 and 8.

Figure 8:
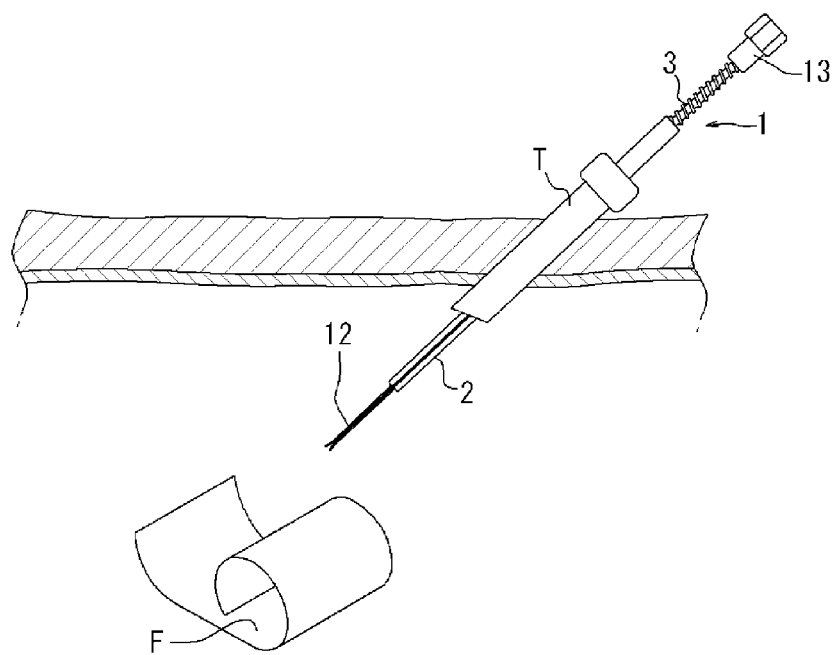
FIG. 8 is a diagram for describing an operation showing a state in which a film is extruded in the body by the device inserted into the body using a trocar.

The mantle tube 2 has a cylindrical tube body 4 of which front and back ends are opened, wherein an outer diameter of the tube body has a size enough to be inserted into a lumen (5.0 mm) of a trocar T (see FIG. 8). Slits 5 having an opposite angle of 180° are formed on a wall facing each other at a front end of the tube body 4 over a predetermined length backward from a front opening. That is, the slit 5 has an axial length L larger than a width of the film F and a circumferential width W having a size enough to have the film F inserted thereinto and can be configured to insert and hold the film F thereinto from the front end. In addition, the back end of the tube body 4 is fitted with one end of a gripping tube 6 having a large diameter.

The extruding member 3 has a hollow shaft 11 for winding and extrusion that is a longer length than the mantle tube 2, a forked film winding part 12 provided at a tip of the shaft, and a gripping tube 13 for operation provided at a back end of the shaft 11. An outer diameter of the shaft 11 is formed to be slightly smaller than an inner diameter of the tube body 4 of the mantle tube 2 and the shaft 11 can be advanced and retreated (moved) in a front and back direction that is a tube-axis direction and can also be rotated in a circumferential direction, in the tube body 4. The film winding part 12 has a shape in which two sheets of plate parts 12a and 12b are disposed to face each other with a gap having a size enough to insert the film F thereinto and the axial length thereof is slightly longer than the axial length L of the slit 5 of the mantle tube 2 and tips thereof have a shape that can be extendedly opened outwardly. The reason why the two tips have the shape that can be extendedly opened is to facilitate the insertion of the film F.

The gap between the plate parts 12a and 12b of the film winding part 12 as described above is aligned with the circumferential direction position of the slit 5 of the mantle tube 2, such that the film F can be inserted between the gap and the slit 5. Both of the width W of the slit 5 of the mantle tube 2 and the gap between the plate parts 12a and 12b of the film winding part 12 are set to be about 1.0 mm. Further, although not illustrated in the present embodiment, a positioning means (for example, the engaging by a concavo-convex shape, and the like) for performing the positioning may be disposed at an appropriate place of the inner circumferential surface of the mantle tube 2 and the outer circumferential surface of the extruding member 3 and the shape thereof and the like may be arbitrarily designed. When the foregoing positioning means is provided, the positioning can be performed in a normal state that is a state before being used and therefore, the film F is easily inserted between the gap between the plate parts 12a and 12b of the film winding part 12 and the slit 5 of the mantle tube 2 and then, the winding work can be rapidly performed.

An outer circumferential surface of a back end of the gripping tube 13 is provided with a gripping part 14 having a large diameter and a polygonal shape so as to be easily picked up by an operator's fingers. Further, a concave part 15 is formed around a back end of the shaft 11 and a helical spring 17 is disposed between the concave part 15 and a concave part 16 formed at the other end of the gripping tube 6 of the mantle tube 2, having the shaft 11 disposed therebetween. The spring 17 is generally in an extended state as illustrated in FIG. 1 and the tips of the plate parts 12a and 12b of the film winding part 12 are slightly protruded from a tip opening of the mantle tube 2.

Figure 6:
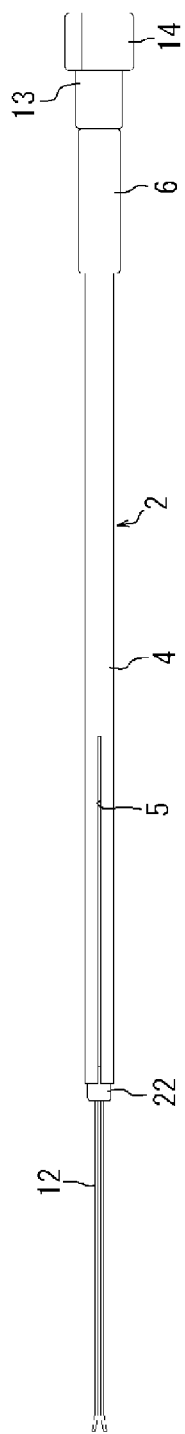
FIG. 6 is a front view illustrating a state in which a shaft is press-fitted in a mantle tube by a gripping part.

In addition, in the state in which the gripping tube 13 is used while closest approaching the gripping tube 6, as illustrated in FIG. 6, almost the whole of the film winding part 12 can be protruded outside the mantle tube 2.

As described above, when the shaft 11 is rotated in the state in which the film F is inserted between the gap of the film winding part 12 and the slit 5 of the mantle tube 2, the film F is wound around the shaft 11 in the form in which the outer circumferential side of the film F is pressed to the tube body 4 of the mantle tube 2 and thus, is simply wound and received within the mantle tube 2. That is, the tube body 4 of the mantle tube 2 has an inner portion formed to be the receiving part of the film F. Further, the wound film F is protruded outside the mantle tube 2 by extruding the shaft 11 forward. At the protruded timing, a winding diameter is increased by repellence due to its own elastic force and when the shaft 11 is returned the film is locked to the front end of the mantle tube 2 and released into an internal cavity.

Figure 5:
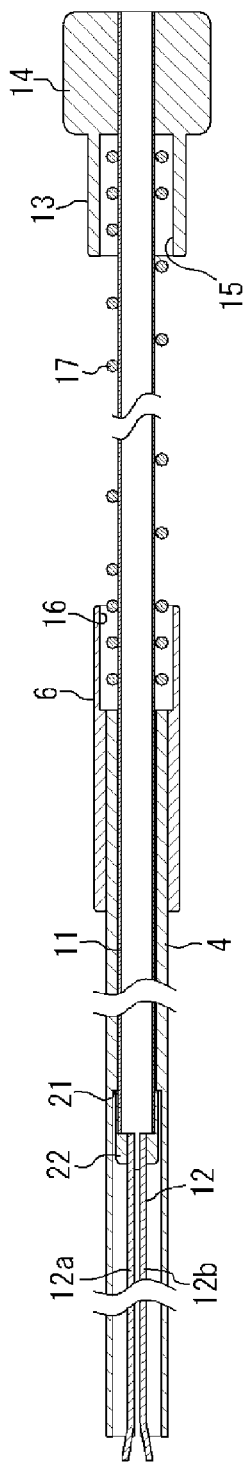
FIG. 5 is an enlarged cross-sectional view illustrating a state in which the device for sheet insertion is partially fractured longitudinally.

In FIG. 5, reference numeral 21 is a locking protrusion that is disposed on an inner circumferential surface of the mantle tube 2, wherein the locking protrusion can lock a locking member 22 that is disposed on the outer circumferential surface of the shaft 11 of the extruding member 3. The locking protrusion 21 and the locking member 22 configure a stopper mechanism of the extruding member 3 and when the film F is inserted and then, the shaft 11 is retreated by an energizing force of a spring 17, the locking member 22 is locked to the locking protrusion 21 to prevent the shaft 11 from being retreated further. The locking member 22 is a fixing part of the film winding part 12, the base end is fitted in the front end of the shaft 11, the tip is provided with two openings having a flat shape, and the base ends of the plate parts 12a and 12b of the film winding part 12 are fixed in two openings. The base ends of the plate parts 12a and 12b are fixed as described above, such that the tips are in an extending state in parallel with each other and the gap is formed between the plate parts 12a and 12b.

A dimension of each part of the device 1 described in the first embodiment will be described below for reference. That is, the axial length of the mantle tube 2 including the gripping tube 6 is about 225 mm, the axial length of the shaft 11 including the gripping tube 13 and the film winding part 12 is about 245 mm, the axial length of the film winding part 12 is about 60 mm, and the axial length of the slit 5 of the mantle tube 2 is about 60 mm. Further, the outer diameter of the mantle tube 2 is about 5 mm, the outer diameter of the gripping tube 6 is about 7 mm, the outer diameter of the gripping tube 13 is about 12 mm, and the outer diameter of the shaft 11 is about 3 mm. Further, as illustrated in FIG. 1, the tip of the film winding part 12 is slightly further protruded than the tip opening of the mantle tube 2 in a normal state and as illustrated in FIG. 6, the base end of the film winding part 12 is protruded from the tip opening of the mantle tube 2 in the state in which the gripping tube 13 is used while closest approaching the gripping tube 6.

Figure 7:
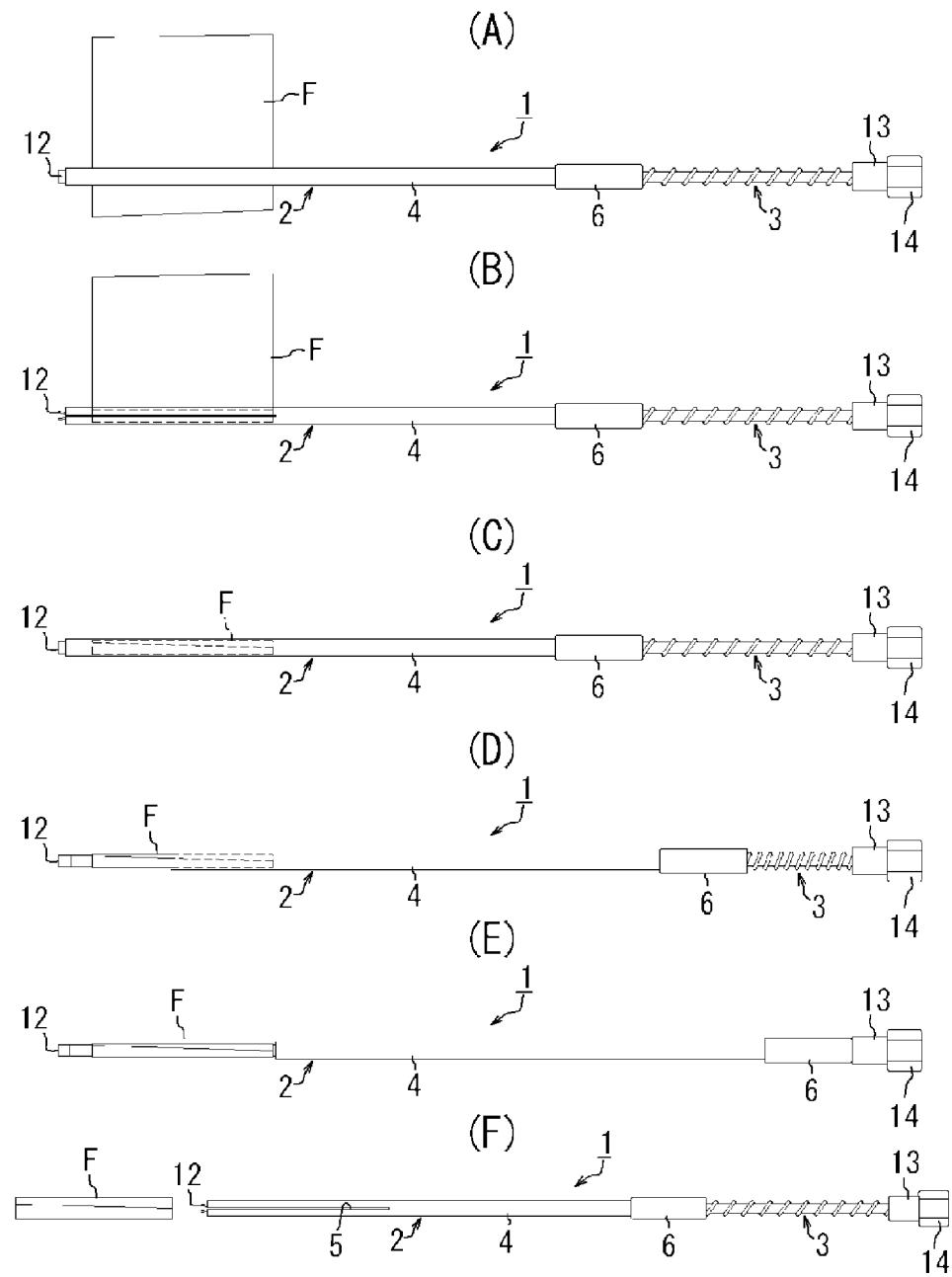
FIGS. 7A to 7F are diagrams for describing an operation.

Next, the use method of the device 1 will be described below with reference to FIGS. 7 and 8.

When using the device 1, as illustrated in FIG. 1, in the state in which the extruding member 3 to which the gripping part is attached is set in the mantle tube 2, the slit 5 of the mantle tube 2 positions the gap of the film winding part 12 of the shaft 11. The positioning is performed by rotating the shaft 11 in the mantle tube 2, but as described above, the positioning may be performed in a normal state by providing the positioning means. After the positioning is performed, the film F cut at a predetermined size in advance is inserted into and passed through the gap of the plate parts 12a and 12b of the film winding part 12 and the slit 5 of the mantle tube 2 and as illustrated in FIG. 7A, the film F is set. In this case, the insertion work of the film F may be more rapidly performed by providing the positioning means.

Next, the shaft 11 is rotated while the mantle tube 2 is gripped by one hand and the gripping tube 13 having the gripping part 14 is gripped by the other hand, to wind the film F around the outer circumference of the film winding part 12. In this case, an operator's hand does not need to touch the film F as in the past and the film may be simply wound around and up. FIG. 7B is a diagram illustrating the state immediately after the winding of the film F starts and FIG. 7C is a diagram illustrating the state in which the winding of the film F is completed. As clearly illustrated in FIG. 7C, when the winding is completed, the whole film F is received in the mantle tube 2.

Further, after the winding of the film F around the film winding part 12 is completed, as illustrated in FIG. 8, the device 1 is inserted into the lumen of the trocar T that is mounted in a body site of a place into which the film F needs to be inserted. Further, the shaft 11 is advanced against the spring 17 by using the gripping part 14 after the insertion and the film F wound around the film winding part 12 is extruded from the mantle tube 2 as it is. FIG. 7D is a diagram illustrating the state in which the film F is being extruded and FIG. 7E is a diagram illustrating the state in which the extruding of the film F is completed. As can be clearly appreciated from FIG. 7E, when the extruding is completed, the back end of the film F is slightly protruded from the front opening end of the mantle tube 2, such that the whole film F is protruded to the outside.

Further, when the extruding is completed and then, the advance of the shaft 11 is released (takes the operator's hands off the gripping part 14) by the gripping part 14, the shaft 11 is returned to an original state by the force of the spring 17 and the back end of the film F is locked to the front opening end of the mantle tube 2 by the returning action of the shaft 11 so that the film F protruded outwardly from the mantle tube 2 is separated from the film winding part 12. Next, after being separated, the film is released by the strength of the elastic force. FIG. 7F is a diagram illustrating the state in which the film F is separated from the film winding part 12 and FIG. 8 is a diagram illustrating an operation state during the operation.

The film F that is in this state is appropriately gripped by the endoscope inserted after the device 1 is removed and is moved to the operation site that is the targeted in vivo site and applied to the diseased site.

As described above, according to the device 1 of the first embodiment, there is no need to touch the operator's hands to the film F as in the past at the time of winding the film F and it is possible to simply insert the film into the targeted in vivo site, thereby very facilitating the insertion operation. Therefore, it is possible to skillfully and simply perform the application or detention of the film F at the targeted site in the endoscopic operation and thus shorten the operation time. Further, the film F can be simply inserted by being locked to the front opening end of the mantle tube 2 by the action of the spring 17 at the time of inserting the film F and the operability is improved. In addition, as in the first embodiment, the device 1 may also be sufficiently used for the trocar having the lumen with a small diameter of 5.0 mm.

Figure 9:
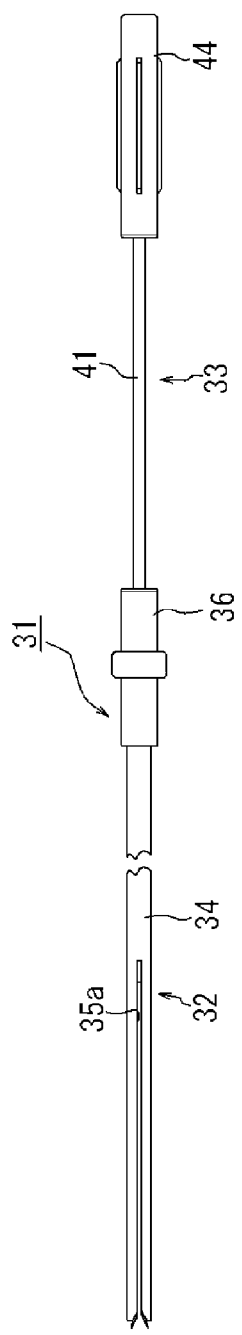
FIG. 9 is a front view illustrating a state in which a device for sheet insertion according to Modification Example 1 of an axial slit is partially fractured longitudinally.
Figure 10:
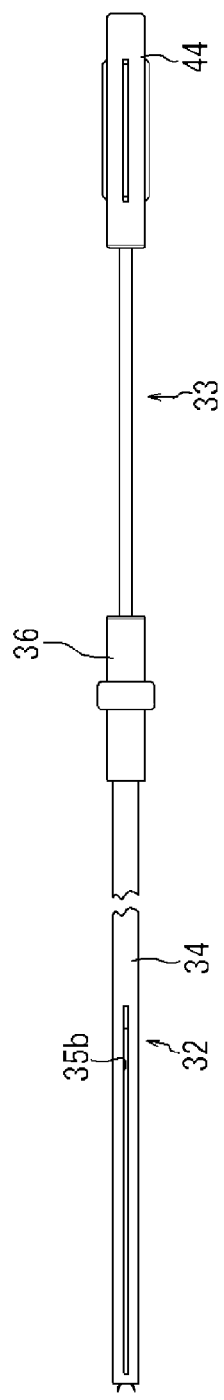
FIG. 10 is a rear view of FIG. 9.
Figure 11:
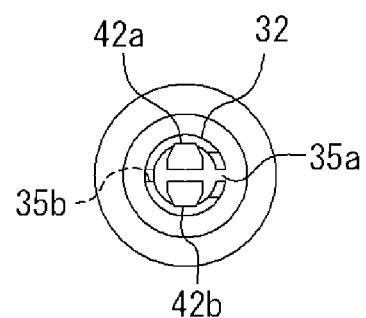
FIG. 11 is an enlarged side view seen from the left of FIG. 10.

FIGS. 9 to 11 illustrate Modification Example 1 of the axial slit. A device 31 for sheet insertion to which Modification Example 1 is applied has a somewhat different shape from the device 1 of the first embodiment, but when viewing only the axial slit, among the axial slits formed on the walls facing each other at the front end of the tube body 34 of the mantle tube 32, slit 35a is formed over approximately the same length as the length of the film winding part 42 from the front opening of a tube body 34 and the other slit 35b is formed over approximately the same length as the length of the film winding part 42 from a position (in other words, a position a predetermined length away from the front opening) at a predetermined length (for example, several mm) from the front opening. That is, in the first embodiment, both axial slits are formed to communicate with the opening from the front opening of the mantle tube 32, while in Modification Example 1, one slit is formed from the position at a predetermined length from the front opening, that is, a slit communicating with the tip opening is set to be one. Further, in the device 31, the helical spring as provided in the device 1 is not inserted into the shaft 41 of the extruding member 33. Other components have a slight difference in a detailed aspect, but do not have a large difference in terms of a function.

For the following reason, the axial slit is configured as described above. That is, the case in which the mantle tube 32 made of metal is used does not cause any problem. However, when the mantle tube 32 is made of synthetic resins softer than metal, it was found that the mantle tube 32 cannot be put into practical use because when the film F is inserted thereinto, the mantle tube cannot be endured due to the thickness of the wound film and the tip portion of the mantle tube 32 is largely opened from the boundary line between the axial slit and the tip opening. Therefore, the walls on which the axial slits are formed are connected in a circumferential direction without forming the gap at the tip of several mm in one slit, such that the one slit may prevent the tip portion of the mantle tube from being opened even in the thickness formed at the time of winding the film.

Figure 12:
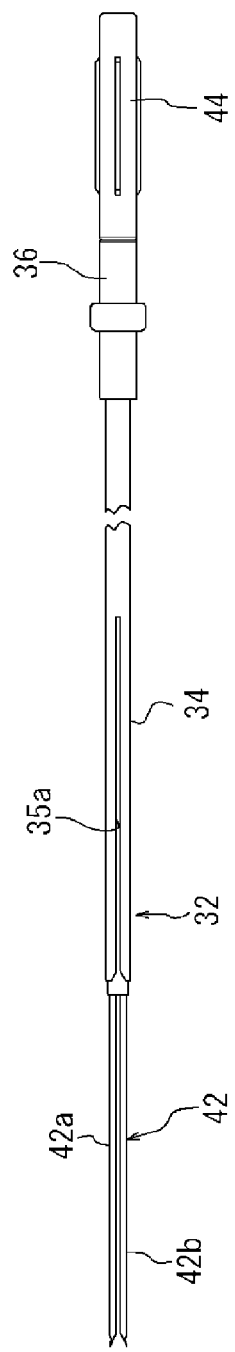
FIG. 12 is a front view illustrating a state in which a shaft is press-fitted in a mantle tube by a gripping part.

In order to insert the film F using the device 31, for example, the film F is obliquely inserted via one slit 35a formed with the slits from the front opening so as to be inserted and set into the gap of the plate parts 42a and 42b of the film winding part 42 and the silt 35b at an opposite side thereto. Further, the set film F is wound around the outer circumference of the film winding part 42 according to the rotation of the shaft 41 and wound up. FIG. 12 illustrates the state in which the film F is wound and then, the shaft 41 is press-fitted and the film winding part 42 is protruded from the tip opening of the mantle tube 32 (the film F is not illustrated). In FIG. 12, reference numeral 44 represents a gripping part and reference numeral 36 represents a gripping tube.

Further, in the device 31, one slit is formed from the tip opening, and the other slit is formed at a predetermined distance from the tip opening, therefore, there is a case in which the operator does not know which of the slits is formed from the tip opening. For this reason, although not specifically illustrated herein, a mark identifying which of the slits is formed from the front opening is put at the mantle tube or the shaft. The mark may be put in the vicinity of the slit from the tip opening or may be put at the slit that is at a predetermined length from the tip opening. Any mark that can be recognized by the operator's eye may be used. When the mark is provided, the operator can instantly recognize the insertion position of the film, thereby rapidly performing the operation.

Figure 13:
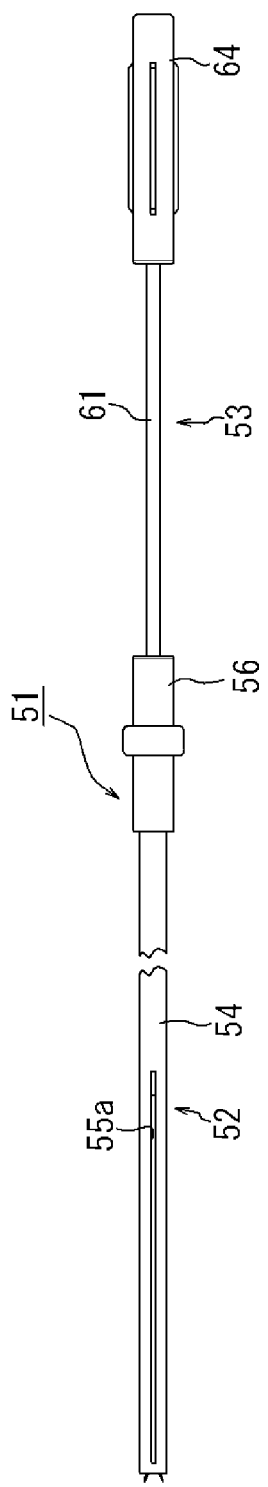
FIG. 13 is a front view illustrating a state in which a device for sheet insertion according to Modification Example 2 of an axial slit is partially fractured longitudinally.
Figure 14:
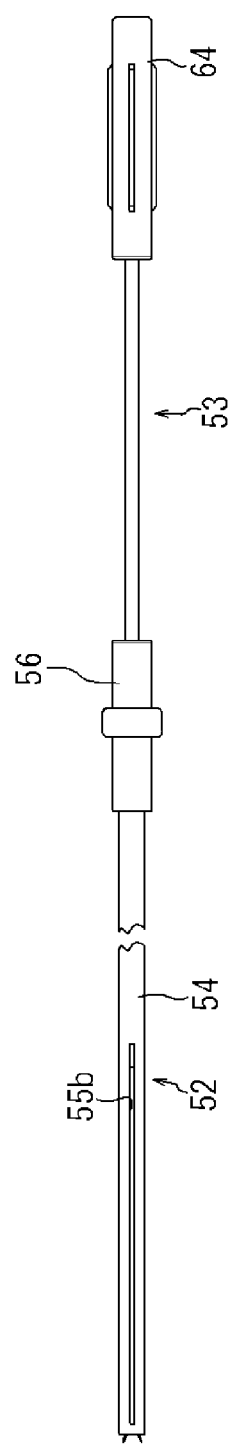
FIG. 14 is a rear view of FIG. 13.
Figure 15:
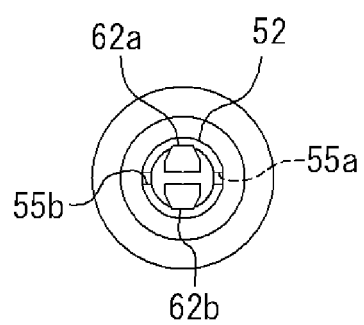
FIG. 15 is an enlarged side view seen from the left of FIG. 14.

FIGS. 13 to 15 illustrate Modification Example 2 of the axial slit. A device 51 for sheet insertion to which Modification Example 2 is applied has approximately the same structure as the device 31 of Modification Example 1 except for the axial slits and therefore, parts similar to the parts in the Modification Example 1 are denoted by the numbers that are obtained by adding 20 to the reference numbers of the Modification Example 1, respectively. That is, in the device 51, both axial slits formed by facing each other at the front end of a tube body 54 of a mantle tube 52, that is, slits 55a and 55b are formed from a position at a predetermined length from the front opening of the tube body 54.

In order to insert the sheet using the device 51, the film F is obliquely inserted from any one slit, for example, the slit 55a so as to be inserted and set into a gap of plate parts 62a and 62b of the film winding part 62 and the silt 55b at an opposite side thereto. Further, the set film F is wound around the outer circumference of the film winding part 62 according to the rotation of the shaft 61 and wound up. Therefore, the film F is wound up around the outer circumference of the film winding part 62, as in the Modification Example 1.

As described above, both the axial slits 55a and 55b of Modification Example 2 are formed from a position at a predetermined length from the front opening and the wall on which the slits are formed is completely connected in a circumferential direction and thus, has a structure without a gap, such that Modification Example 2 has the larger strength of the axial slits and is resistant to tensile rupture, as compared with Modification Example 1 having the form in which only the wall on which one slit 35b is formed is connected in a circumferential direction.

Second Embodiment

Figure 16:
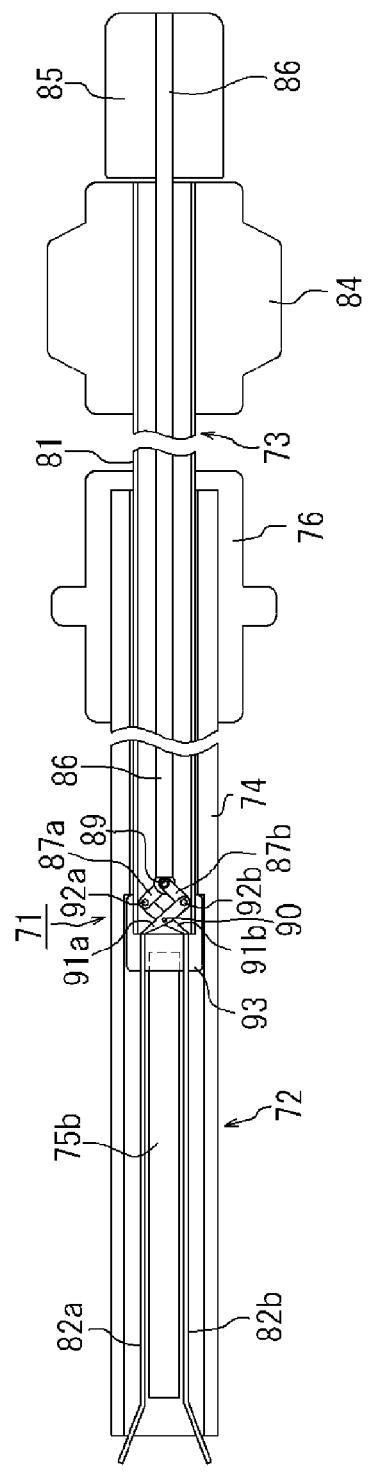
FIG. 16 is an enlarged front cross-sectional view illustrating a state in which a device for sheet insertion according to the second embodiment of the present invention is partially fractured longitudinally and illustrates a state in which a tip of a film winding part is opened.
Figure 17:
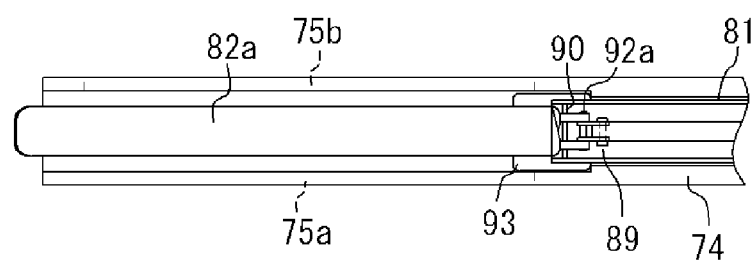
FIG. 17 is an enlarged side cross-sectional view illustrating only a tip.
Figure 18:
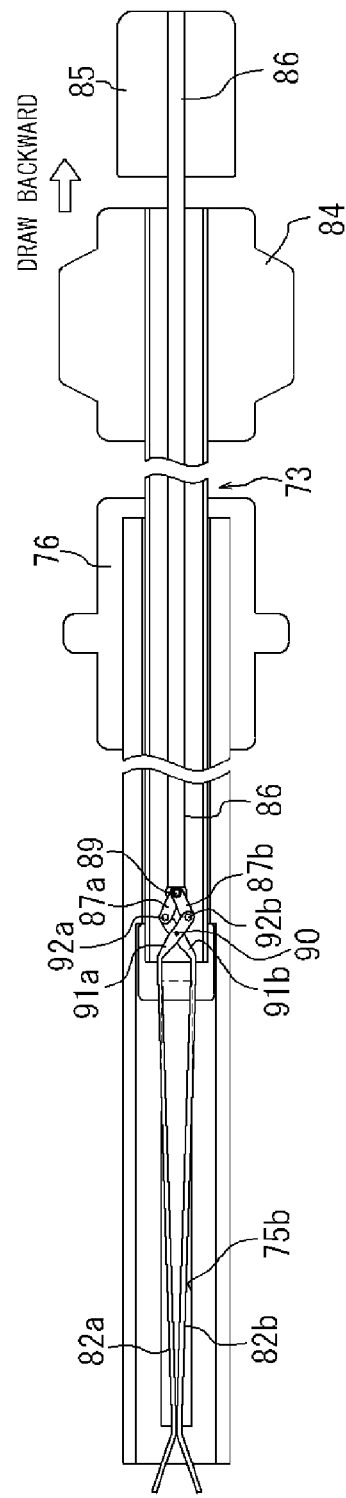
FIG. 18 is an enlarged front cross-sectional view illustrating a state in which the device is partially fractured longitudinally and illustrates a state in which the tip of the film winding part is closed.

FIGS. 16 to 18 illustrate second embodiment. A device 71 for sheet insertion according to the second embodiment is similarly to the Modification Example 2 at a point that one slit 75a of the axial slits is formed over approximately the same length as that of a film winding part 82 from a front opening of a tube body 74 and the other slit 75b is formed over approximately the same length as that of the film winding part 82 from a position at a predetermined length from the front opening, but is different from the Modification Example 2 at a point that the device 71 has a structure of a so-called pincette type into which the film F is inserted. Other parts are the same as those in the Modification Example 2 and therefore, parts similar to the parts in the Modification Example 2 are denoted by the numbers that are obtained by adding 20 to the reference numbers of the Modification Example 2, respectively.

That is, the device 71 according to the second embodiment includes a shaft gripping part 85 with a film winding part, the gripping part being provided with a shaft 86 having a tip that passes through a shaft gripping part 84 and the inside of the tube body of the mantle tube and extends to a locking member 93 that is movably provided within the tube body. The tip of the shaft 86 is pivoted with a first same length link 87a and a second same length link 87b by a base shaft 89 and the tips of the first same length link 87a and the second same length link 87b are pivoted with back ends of same length arms 91a and 91b, which are pivoted by a fixing shaft 90 in an intermediate part, by connection shafts 92a and 92b. Both ends of the fixing shaft 90 are fixed to a circumferential wall on which a lumen of a locking member 93 exists.

In addition, tips of the same length arms 91a and 91b are fixed with the back ends of the plate parts 82a and 82b of the film winding part 82. Therefore, when the shaft gripping part 85 is drawn, as shown by an arrow of FIG. 18, backwardly from the state in which the tips of the plate parts 82a and 82b are opened as illustrated in FIGS. 16 and 17 by holding the gripping part 84, at the same time, the shaft 86 is also drawn and the first same length link 87a and the second same length link 87b are pressed inwardly by the shaft 86. Therefore, the back ends of the plate parts 82a and 82b of the film winding part 82 are pressed inwardly and the tips of the plate parts 82a and 82b approach each other toward an inner side like a pincette to close the plate parts 82a and 82b inward (state of FIG. 18) such that the film F inserted between the plate parts 82a and 82b can be sandwiched so as to be wound up.

Further, in order to again open the plate parts 82a and 82b of the film winding part 82, the shaft gripping part 85 is press-fitted to return to the original state by holding the drawn shaft gripping part 84. Simultaneously, the first same length link 87a and the second same length link 87b are pressed outwardly by the shaft 86 that are press-fitted and the back ends of the plate parts 82a and 82b are also pressed outwardly to return the tips thereof to the opened state as illustrated in FIGS. 16 and 17.

Therefore, in the second embodiment, the film F can be simply wound around the outer circumference of the film winding part 12 and the tips of the plate parts 82a and 82b of the film winding part 82 can be opened and closed by moving the shaft 86 back and forth by the operation of the shaft gripping part 85, as in the first embodiment and the tips are closed to certainly sandwich the film F, such that the film F can be guided to the targeted site without missing the film within the body cavity. For this reason, it is possible to skillfully and simply perform the application or detention of the sheet at the targeted site and shorten the operation time.

As described above, the devices described in the first and second embodiments or Modification Examples 1 and 2 are only preferred examples and therefore, the detailed design of the present invention can be arbitrarily changed and modified within the scope of the appended claims. The mark confirming which of the axial slits is formed from the front opening is described only for the device of Modification Example 2, but the mark can be definitely applied to devices according to other Modification Examples or Embodiments.

The invention claimed is:

1. A device for sheet insertion used to insert a sheet of a synthetic absorbable anti-adhesion sheet and the like into a targeted in vivo site through a lumen of a trocar in an endoscopic operation, comprising:
   a cylindrical mantle tube of which front and back ends are opened and inside is formed to be a sheet receiving part, and an extruding member for extruding a sheet, the extruding member being inserted into the mantle tube in a state of moving in a back and forth direction that is a tube-axis direction and of rotatable,
   wherein the extruding member has a shaft having a longer length than that of the mantle tube, a forked sheet winding part disposed at a tip portion of the shaft, and a gripping part for operation disposed at a back end of the shaft, the sheet winding part is received in the mantle tube by a movement of the extruding member backward, the sheet winding part being protruded from a front opening of the mantle tube by a movement of the extruding member forward; and the mantle tube has axial slits having a size enough to insert the sheet therethrough, which are formed on walls facing each other at the front end of the mantle tube over approximately the same length as a length of the sheet winding part, wherein a stopper mechanism, including a first locking member disposed on the inner circumferential surface of the mantle tube and a second locking member disposed on the outer circumferential surface of the shaft of the extruding member, locks the second locking member to the first locking member by a movement of the shaft backward to prevent the shaft from moving backward further.

2. The device for sheet insertion according to claim 1, wherein a pressing member pressing a sheet winding part of the extruding member so as to be received in a sheet receiving part within the mantle tube is disposed between a gripping part of the extruding member and a back end of the mantle tube, and when the extruding member is moved forward while being press-fitted into the mantle tube, the pressing member is pressed to protrude the sheet winding part outwardly from the mantle tube and when the extruding is moved backward, the pressing member extends to receive the sheet winding part in the mantle tube.

3. The device for sheet insertion according to claim 1, wherein the sheet winding part of the extruding member has two parts disposed to face each other, with a gap having a size enough to insert the sheet therebetween and an axial length thereof is slightly longer than that of a slit of the mantle tube and a tip thereof is extendedly opened.

4. The device for sheet insertion according to claim 1, wherein a positioning means positioning the slit of the mantle tube and the gap of the sheet winding part of the shaft in a circumferential direction are disposed on an inner circumferential surface of the mantle tube and an outer circumferential surface of the shaft of the extruding member.

5. The device for sheet insertion according to claim 1, wherein both the axial slits facing each other are formed over approximately the same length as that of the sheet winding part from a front opening of the mantle tube.

6. The device for sheet insertion according to claim 1, wherein one slit of the axial slits facing each other is formed over approximately the same length as that of the sheet winding part from the front opening of the mantle tube and the other slit is formed over approximately the same length as that of the sheet winding part from a position at a predetermined length from the front opening.

7. The device for sheet insertion according to claim 1, wherein both the axial slits facing each other are formed over approximately the same length as that of the sheet winding part from a position at a predetermined length from a front opening of the mantle tube.

8. The device for sheet insertion according to claim 1, wherein a mark identifying a position at which the axial slit is formed is put on the mantle tube or the shaft.

9. The device for sheet insertion according to claim 1, further comprising:
   wherein the gripping part includes a second shaft having a tip extending into the mantle tube, the tip of the second shaft is pivoted with base ends of a pair of links having the same length, the tips of the links having the same length are pivoted with back ends of a pair of arms having the same length that is pivoted to the shaft having an intermediate part disposed on the extruding member, the tips of the arms are fixed with back ends of two plate parts of the sheet winding part, and when the second shaft is drawn backward, the two links having the same length and the two arms having the same length are pressed inwardly and the back ends of two plate parts of the sheet winding part are also pressed inwardly, such that the tips of the two plate parts are changed from an opened state to a closed state.

\* \* \* \* \*